United States Patent [19]

Stout et al.

[11] Patent Number: 4,657,919

[45] Date of Patent: Apr. 14, 1987

[54] PYRIDONE ESTERS AS INOTROPIC AGENTS

[75] Inventors: David M. Stout, Vernon Hills; Diane M. Yamamoto, Gurnee, both of Ill.; Cynthia Barcelon-Yang, Kenosha, Wis.

[73] Assignee: E. I. Du Pont de Nemours & Co., Wilmington, Del.

[21] Appl. No.: 754,322

[22] Filed: Jul. 12, 1985

Related U.S. Application Data

[63] Continuation-in-part of Ser. No. 637,352, Aug. 3, 1984, Pat. No. 4,555,517.

[51] Int. Cl.$^4$ .................. C07D 401/06; A61K 31/44
[52] U.S. Cl. ..................................... 514/335; 546/261
[58] Field of Search .............. 546/296, 297, 261, 298, 546/299, 288, 283, 278, 275, 256, 284, 153, 157, 140, 141; 544/238, 296, 316, 318, 319, 284, 237; 514/248, 253, 274, 269, 309, 314, 341, 348, 344, 350, 349, 374, 397, 335

[56] References Cited

U.S. PATENT DOCUMENTS

| | | | |
|---|---|---|---|
| 3,853,897 | 12/1974 | Witzel et al. | 546/290 |
| 4,412,077 | 10/1983 | Lesher et al. | 546/298 |
| 4,415,580 | 11/1983 | Lesher et al. | 546/298 |
| 4,447,619 | 5/1984 | Grisar et al. | 548/318 |
| 4,469,699 | 9/1984 | Lesher et al. | 546/280 |
| 4,517,192 | 5/1985 | Lesher | 546/288 |
| 4,530,842 | 7/1985 | Bormann | 548/288 |

FOREIGN PATENT DOCUMENTS 0124090  7/1984  European Pat. Off. .
0124089 11/1984  European Pat. Off. .

OTHER PUBLICATIONS

Opgenorth et al, CA 90:54840a.
Sunthankar et al, CA vol. 80, 133202r.
Hirota et al, CA 94:103325e.
Duffield et al. CA vol. 65, 3152f.
Harris et al, CA vol. 64, 18224d.
Badische, CA vol. 64, 9694h.
Neuhoff et al, CA 7540g, vol. 61.
Arnold et al. CA 7725i, 1962.
Hirota et al. Chem. Abs.. vol. 95, 1981, 95:132434r.
Sano et al., Chem. Abst., vol. 88, 1978, 88:169907d.
Anghelide et al., Chem. Abst., vol. 81, 1974, 77429b.
Baker et al, J. Chem. Soc. Perkin Trans. I. (3) 1979, pp. 677-685.
DeJohn et al, J. Het. Chem. 20, 1295, 1983, Hawald et al.
Indian, J. Chem. Sect. B, 19B (2), 151-152, 1980.
Sunthankav et al, Ind. J. Chem. 1973, 11(12) pp. 1315-1316.
Scott et al, CA 90:174685a.
Hirota et al, CA 102:184956v.

*Primary Examiner*—Jane T. Fan
*Attorney, Agent, or Firm*—Gildo E. Fato

[57] ABSTRACT

Described are compounds of the formula

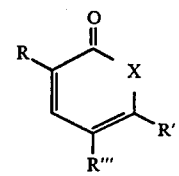

wherein R is hydrogen, lower alkyl, halo, cyano, hydroxy, amino, lower alkylamino, —CH$_2$NH$_2$, —CH$_2$OH or —COOR''; R' is hydrogen, lower cycloalkyl or lower alkenyl, lower alkynyl, lower cycloalkyl, —(W)$_n$Y wherein W is straight or branched chain lower alkyl or lower alkenyl, n is 0 to 5, and Y is Ar, lower cycloalkyl, lower alkenyl, lower alkynyl, —COOZ wherein Z is lower alkyl,

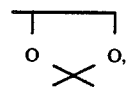

or NAB wherein A and B are, independently, lower alkyl, benzyl or substituted benzyl, and Ar is 2, 3 or 4-pyridyl, pyridazinyl, pyrimidinyl, quinolyl, isoquinolyl, phthalazinyl, quinazolinyl, thiazolyl, phenyl, benzyl, furyl, tetrahydrofuryl or thienyl, unsubstituted or substituted with lower alkyl, lower alkoxy, halo, amino, or —CF$_3$; R''' is —COOR'',

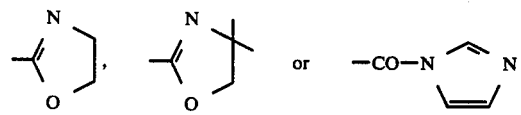

and X is oxygen or nitrogen; or a pharmaceutically acceptable salt thereof, and their use in the treatment of impaired ventricular myocardial contractility.

The compounds exhibit cardiotonic activity.

2 Claims, No Drawings

PYRIDONE ESTERS AS INOTROPIC AGENTS

This application is a continuation-in-part of Ser. No. 637,352, filed Aug. 3, 1984, now U.S. Pat. No. 4,555,517 issued Nov. 26, 1985.

BACKGROUND OF THE INVENTION

Cardiotonic agents have been used for the treatment of heart failure for some time with digital is continuing to be one of the principle pharmacologic agents used for this purpose, although the cardiac glycosides in a class do have some limitations. Cardiac output is regulated by the integration of the contractile state of the heart and the dynamics of the peripheral circulatory system. When the heart fails, the primary problem is impairment of ventricular myocardial contractility which results in inadequate cardiac output to meet the metabolic and circulatory demands of the body. Effective therapy of heart failure is accomplished by either enhancing the contractile state of the heart with positive inotropic agents, or by adjusting the peripheral circulatory state with peripheral vasodilators. Agents which stimulate myocardial contractility are of considerable value in the treatment of heart failure. Conventional therapy for heart failure has been the use of digitals preparations which are the only orally effective inotropic drugs available for use in the treatment of this condition. However, their peripheral vascular effects are undesirable. Sympathomimetic amines are the other major class of cardiac stimulants which are used for the treatment of heart failure. The use of these agents is likewise limited, because they are not fully effective when administered orally and because of undesirable peripheral vasoconstrictor action. Currently, dobutamine and dopamine are the sympathomimetic agents which are primarily used for heart failure, but they can only be administered parenterally.

Several promising inotropic agents which have been studied clinically are the pyridones, amrinone and milrinone, having the following formula:

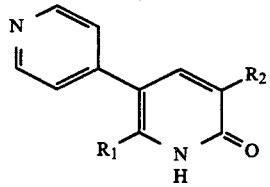

Amrinone: $R_1 = H$; $R_2 = NH_2$; Milrinone; $R_1 = CH_3$; $R_2 = CN$.

Amrinone is effective in treating patients with heart failure but its use has been severely restricted to acute use only because it has been associated with a high incidence of serious side effects.

Milrinone is undergoing clinical testing as an inotropic agent and its usefulness has not yet been established.

Because of the limitations of currently available drugs in the treatment of heart failure, there is a clear need for new, effective and safe drugs of this type.

SUMMARY OF THE INVENTION

The present invention is directed to compounds of the formula

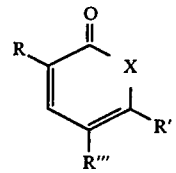

wherein R is hydrogen, lower alkyl, halo, cyano, hydroxy, amino, lower alkylamino, —CH$_2$NH$_2$, —CH$_2$OH or —COOR''; R' is hydrogen, lower cycloalkyl or lower alkyl; R'' is lower alkenyl, lower alkynyl, lower cycloalkyl, —(W)$_n$Y wherein W is straight or branched chain loweralkyl or lower alkenyl, n is 0 to 5, and Y is Ar, lower cycloalkyl, lower alkenyl, lower alkynyl, —COOZ wherein Z is lower alkyl, $$\begin{array}{c} \text{O} \diagdown \diagup \text{O,} \\ \times \end{array}$$

or NAB wherein A and B are, independently, lower alkyl, benzyl or substituted benzyl, and Ar is 2, 3 or 4-pyridyl, pyridazinyl, pyrimidinyl, quinolyl, isoquinolyl, phthalazinyl, quinazolinyl, thiazolyl, phenyl, benzyl, furyl, tetrahydrofuryl or thienyl, unsubstituted or substituted with lower alkyl, lower alkoxy, halo, amino, or —CF$_3$; R''' is —COOR''.

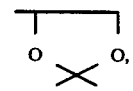

and X is oxygen or nitrogen; or a pharmaceutically acceptable salt thereof, and their use in the treatment of cardiac disorders, and in particular, in providing a positive inotropic effect in the treatment of impaired ventricular myocardial contractility.

The term "lower alkyl" as used herein refers to straight or branched chain alkyl radicals containing from 1 to 6 carbon atoms including but not limited to methyl, ethyl, n-propyl, iso-propyl, n-butyl, sec-butyl, 2-methylhexyl, n-pentyl, 1-methylbutyl, 2,2-dimethylbutyl, 2-methylpentyl, 2,2-dimethylpropyl, n-hexyl and the like.

The term "lower cycloalkyl" as used herein refers to cyclic saturated aliphatic radicals containing 3 to 6 carbon atoms in the ring, such as cyclopropyl, cyclobutyl, cyclopentyl or cyclohexyl.

The term "halo" includes chloro, fluoro, bromo and iodo.

The term "substituted phenyl" represents phenyl which may be substituted with lower alkyl, halo, hydroxy, alkoxy or amino.

The term "pharmaceutically acceptable salts" includes nontoxic acid addition salts of the compounds of the invention which are generally prepared by reacting the free base with a suitable organic or inorganic acid. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, and like salts. Also included are metallic salts such as the sodium or potassium salt of the acid.

The present compounds may be administered to warm-blooded animals orally or parenterally. They can generally be administered with a pharmaueutical carrier. The term "pharmaceutical carrier," for the purpose of the present invention, is intended to refer to any medium that is suitable for the preparation of a dosage unit form, and, thus, includes the tablet medium or a pharmaceutically acceptable vehicle or solvent such as is ordinarily used in the preparation of intravenous or intramuscular solutions.

A pharmaceutical composition containing the compound can be administered to warm-blooded animals in parenteral or oral dosage form. For parenteral administration, amounts of from about 10 to 100 mg/kg per day per patient are useful, with the total dose of up to 0.2 to 2 grams per day being a suitable range for large animals, including humans. A preferred dosage range is from about 1 to 10 grams total daily dosage in a single or divided dose.

For all dosage forms the above exemplified compounds can be placed in capsules, formulated into pills, wafers, or tablets in conventional fashion together with pharmaceutical carriers well known in the art. Tablets may be prepared for immediate release of the active compound or they may be made enteric, i.e., whereby the active ingredient is released slowly over a period of several hours from within the intestinal tract.

DETAILED DESCRIPTION OF THE INVENTION

In order to illustrate the manner in which the above compounds may be prepared and the properties of the compounds, reference is made to the following examples, which, however, are not meant to limit or restrict the scope of the invention in any respect.

In the following examples, melting points were obtained on a Thomas-Hoover melting point appatus and are uncorrected. NMR spectra were obtained on a Varian T-60A spectrometer. IR spectra were obtained on a Perkin-Elmer 283 spectrometer. Examples 1 through 5 describe the preparation of intermediates:

EXAMPLE 1

Ethyl ethoxymethyleneacetoacetate (1): Using the procedure of Crombie et al., *Journ. of Chem. Soc. Perkin Trans.* 1, 464–471 (1979), a solution of ethyl acetoacetate (26 g, 0.20 mol), triethyl orthoformate (29.6 g, 0.20 mol) and acetic anhydride (41 g, 0.40 mol) was refluxed for 90 minutes. Distillation under reduced pressure gave the product (1): 26 g, 70% yield; bp=85°–98° C. at 0.5 mm Hg (The following value is reported in the Crombie et al. publication: bp=85° C. at 0.25 mm Hg); NMR (CDCl$_3$) δ 1.2–1.5 (m, 6H), 2.4–2.5 (d,3H), 4.0–4.6 (m,4H), 7.7 (d,1H). The signals were split into pairs of closely spaced lines indicative of the cis and trans isomers.

Using the method of Example 1, the following intermediates were prepared.

EXAMPLE 2

Methyl methoxymethyleneacetoacetate (2): From methyl acetoacetate (30.2 g, 0.26 mol), trimethyl orthoformate (26.7 g, 0.18 mol) and acetic anhydride (53 g., 0.52 mol): 4.3 g, 15%; bp=100°–105° C. at 0.5 mm Hg (lit.[1] 80°–84° C. at 0.15 mm Hg); NMR (CDCl$_3$) δ 2.4 (d, 3H), 3.8 (d, 3H), 4.1 (s, 3H), 7.6 (d, 1H).

EXAMPLE 3

Isopropyl ethoxymethyleneacetoacetate (3): From isopropyl acetoacetate (28.8 g, 0.20 mol) which can be made by the process described by Lawesson etal., *Organic Synthesis*, Coll. Vol. V, 155-157 (1973), triethyl orthoformate (29.6 g, 0.20 mol) and acetic anhydride (41 g, 0.40 mol): 14.3 g, 35.7%; bp=85°–90° C. at 0.20 mm Hg; NMR (CDCl$_3$) δ 1.3–1.6 (m, 9H), 2.3–2.6 (d, 3H), 4.1–4.5 (m, 2H), 5.0–5.4 (m, 1H), 7.6–7.8 (d, 1H).

EXAMPLE 4

Benzyl ethoxymethyleneacetoacetate (4): From benzyl acetoacetate (38.4 g, 0.20 mol), triethyl orthoformate (29.6 g, 0.20 mol) and acetic anhydride (41 g, 0.40 mol): 10.7 g, 21.5%; bp=170°–183° C. at 0.5 mm Hg; NMR (CDCl$_3$) δ 1.0–1.4 (t, 3H), 2.2–2.3 (d, 3H), 4.0–4.4 (q, 2H), 5.2 (d, 2H), 7.4 (s, 5H), 7.8–8.0 (d, 1H).

EXAMPLE 5

Ethoxymethyleneacetylacetone (5): From acethylacetone (20 g, 0.20 mol), triethyl orthoformate (29.6 g, 0.20 mol) and acetic anhydride (41 g, 0.40 mol): 19.3 g, 62%; bp=95°–110° C. at 0.3 mm Hg; NMR (CDCl$_3$) δ 1.3–1.6 (t, 3H), 2.4 (d, 6H), 4.3–4.5 (q, 2H), 7.8 (d, 1H).

EXAMPLE 6

Ethyl 3-cyano-6-methyl-2-pyridone-5-carboxylate (6): Following the procedure described by Sunthanker et al., *Indian Journ. of Chem.* 11 (12), 1315–1316 (1973), to a solution of sodium metal (2.3 g, 0.1 g-atom) in ethanol (50 ml) was added slowly with stirring an ethanolic solution (200 ml) of cyanoacetamide (8.4 g, 0.1 mol). The reaction mixture was stirred for about 5 minutes, after which an ethanolic solution (20 ml) of compound 1 (18.6 g, 0.1 mol) was added. The mixture was stirred for 10 minutes during which time it became turbid, yellow and warm. The mixture was refluxed for 45 minutes. Ethanol was then removed under reduced pressure leaving the yellow sodium salt residue. This was dissolved in 50 ml water (with heating) and acidified with 6N HCl to pH 2-3 in an ice bath. The off-whitesolids that precipitated out were filtered and washed with cold water until the filtrate was no longer acidic. The cyclization was done by refluxing the solids in 600 ml of 95% ethanol for two hours. After cooling to room temperature for 18 hours, white crystals precipitated out. These were filtered and washed with cold ethanol. More of the product was obtained by concentrating the filtrate under reduced pressure. A total of 11.5 g (56% yield) was obtained: mp=214°–216° C.; NMR (DMSO-d$_6$) δ 1.3–1.5 (t, 3H), 2.7 (s, 3H), 3.2–3.3 (NH), 4.1–4.5 (q, 2H), 8.5 (s, 1H); IR (KBr) 2220 cm$^{-1}$(CN), 1640–1710 cm$^{-1}$ (C=O of pyridone and ester).

The following compounds were prepared in a manner similar to that described in Example 6.

EXAMPLE 6

Methyl 3-cyano-6-methyl-2-pyridone-5-carboxylate (7): From cyanoacetamide (0.02 mol), sodium metal (0.02 g-atom) in MeOH (20 ml) and 2 (0.02 mol): 0.8 g, 21% yield; mp=281°–283° C. (decomposed); NMR (DMSO-d$_6$) δ 2.6 (s, 3H), 3.2 (NH, OH), 3.8 (s, 3H), 8.4 (s, 1H); IR (KBr) 2220 cm$^{-1}$ (CN), 1650 cm$^{-1}$ (C=O of pyridone), 1700–1720 cm$^{-1}$ (C=O) of ester).

EXAMPLE 8

Isopropyl 3-cyano-6-methyl-2-pyridone-5-carboxylate (8): From cyanoacetamide (0.032 mol), sodium isopropoxide (0.032 mol) and 3 (0.032 mol): 1.3 g, 18% yield; mp=237°–8° C.; NMR (DMSO-$d_6$) δ 1.2–1.4 (2s, 6H), 2.6 (s, 3H), 3.2–3.4 (NH), 4.8–5.2 (m, 1H), 8.4 (s, 1H); IR (KBr) 2220 cm$^{-1}$ (CN), 1660 cm$^{-1}$ (C=O of pyridone), 1700 cm$^{-1}$ (C=O of ester). The NMR showed presence of approximately 20–25% of the compound of Example 6.

EXAMPLE 9 n-Butyl 3-cyano-6-methyl-2-pyridone-5-carboxylate (9): mp 183°–185° C.

EXAMPLE 10 sec-Butyl 3-cyano-6-methyl-2-pyridone-5-carboxylate (10): mp 228.8° C.

EXAMPLE 11

Isobutyl 3-cyano-6-methyl-2-pyridone-5-carboxylate (11): mp 192.9° C. (decomposed)

EXAMPLE 12

Isopentyl 3-cyano-6-methyl-2-pyridone-5-carboxylate (12): mp 203.2° C. (decomposed)

EXAMPLE 13 n-Octyl 3-cyano-6-methyl-2-pyridone-5-carboxylate (13): mp 162.9° C.

EXAMPLE 14

Cyclopentyl 3-cyano-6-methyl-2-pyridone-5-carboxylate (14): mp 248.4° C. (decomposed)

EXAMPLE 15

Cyclohexyl 3-cyano-6-methyl-2-pyridone-5-carboxylate(15): mp 233.8° C. (decomposed)

EXAMPLE 16

Cyclopropylmethyl 3-cyano-6-methyl-2-pyridone-5-carboxylate (16): mp 203.6° C. (decomposed)

EXAMPLE 17

Cyclohexylmethyl 3-cyano-6-methyl-2-pyridone-5-carboxylate (17): mp 235.1° C. (decomposed)

EXAMPLE 18

2 Furylmethyl 3-cyano-6-methyl-2-pyridone-5-carboxylate (18): mp 191.2° C. (decomposed)

EXAMPLE 19

(3-Methyl)-benzyl 3-cyano-6-methyl-2-pyridone-5-carboxylate (19): mp 213° C. (decomposed)

EXAMPLE 20

(4-Trifluoromethyl)benzyl 3-cyano-6-methyl-2-pyridone-5-carboxylate (20): mp 221.2° C.

EXAMPLE 21

5-Acetyl-3-cyano-6-methyl-2-pyridone (21): From cyanoacetamide (0.02 mol), sodium metal (0.02 g-atom) in MeOH (10 ml), and 5 (0.02 mol): 1.0 g, 28% yield; mp=233°–4° C.; NMR (DMSO-$d_6$) δ 2.5 (s, 3H), 2.6 (s, 3H), 8.8 (s, 1H); IR (KBr), 1660 cm$^{-1}$ (C=O of pyridone), 1690 cm$^{-1}$ (C=O of ketone).

EXAMPLE 22

Benzyl 3-cyano-6-methyl-2-pyridone-5-carboxylate (22): Using the method described by Hawalder et al., *Indian Journ. of Chem.*, Sect. B, 19B (2), 151–152 (1980) a mixture of compound 4 (2.5 g, 0.01 mol), cyanoacetamide (0.84 g, 0.01 mol), triethylbenzylammonium chloride (TEBA, 1.1 g 0.005 mol) and 50% NaOH solution (2 ml) was stirred for about 4 hours. The reaction was exothermic and became bright organe. The initially clear solution immediately solidified. A small amount of water was added to facilitate stirring. The mixture was then acidified with 6N HCl, the solids filtered and washed with water and methanol (MeOH) successively. A total of 0.94 g (35%) of off-white solids was obtained: mp=265°–270° C.; NMR (DMSO-$d_6$) δ 2.6 (s, 3H), 3.2–3.5 (NH), 5.4 (s, 2H), 7.4 (s, 5H), 8.6 (s, 1H); IR (KBr) 2240 cm$^{-1}$ (CN), 1660 cm$^{-1}$ (C=O of pyridone), 1730 cm$^{-1}$ (C=O of ester).

EXAMPLE 23

3-Cyano-6-methyl-2-pyridone-5-carboxylic acid (23): This compound was synthesized in the same manner as the compound of Example 22 from cyanoacetamide (0.01 mol), TEBA (0.005 mol), 1 (0.01 mol) and 50% NaOH solution (2 ml). A more efficient method of preparing this compound was refluxing the compound 6 (0.3 g, 1.5 mmol) with NaOH solution (1 ml, 50%) for 1 hour. White solids precipitated out when the solution was acidified with 6N HCl to pH=1. These solids were filtered, washed thoroughly with water and dried to give 0.24 g (90% yield) of the product: mp=285°–287° C. with decomposition; NMR (DMSO-$d_6$) δ 2.6 (s, 3H), 8.4 (s, 1H); IR (KBr) 2220 cm$^{-1}$ (CN), 1640–1660 cm$^{-1}$ (C=O of pyridone), 1710 cm$^{-1}$ (C=O of carboxylic acid).

EXAMPLE 24

3-(Methoxycarbonyl)-5-(ethoxycarbonyl)-6-methyl-2-pyrone (24a) and 3-(Methoxycarbonyl-5-(ethoxycarbonyl)-6-methyl-2-pyridone (24b): Using the procedure described by Baker et al., *Journ. of Chem. Soc. Perkin Trans.* I, 3, 677–685 (1979), ethyl cyanoacetate (3.5 g, 0.031 mol) was added to NaOMe solution (prepared from 0.72 g of sodium metal in 50 ml of MeOH), followed by 1 (5.77 g, 0.031 mol). The mixture was refluxed for 15 minutes, cooled and divided into two equal parts. The first portion was acidified with 2N HCl to pH 2–3 and extracted with $CH_2Cl_2$. The extracts were washed, dried over $MgSO_4$, and evaporated to give an orange-colored solid. After decolorizing with Nuchar activated carbon in ethyl aacetate and recrystallizing from EtOAc-hexane, white, fluffy crystals, of 3-(methoxycarbonyl)-5-(ethoxycarbonyl)-6-methyl-2-pyrone were obtained: 0.22 g, 6% yield; mp=94°–96° C.; NMR (DMSO-$d_6$) δ 1.2–1.5 (t, 3H), 2.7 (s, 3H), 3.8 (s, 3H), 4.1–4.6 (q, 2H), 8.5 (s, 1H); IR (KBr) 1700–1730 cm$^{-1}$ (C=O of Me and Et ester), 1770 cm$^{-1}$ (C=O of pyrone).

The second portion was treated with glacial acetic acid (0.8 ml) and refluxed for 2 hours. Some solids which formed during the reaction were filtered off. The filtrate was acidified with 6N HCl to pH=1–2, precipitating out the desired pyridone as an orange solid. Purification of this solid with Nuchar activated carbon and recrystallization from MeOH-ether gave white, fluffy crystals of 3-(methoxycarbonyl)-5-(ethoxycarbonyl)-6-methyl-2-pyridone: 0.15 g, 4% yield; mp=200°–202°

C.; NMR (DMSO-d$_6$) δ 1.2–1.5 (t, 3H), 2.6 (s, 3H), 3.8 (s, 3H), 4.1–4.4 (q, 2H), 8.6 (s, 1H); IR (KBr) 1660 cm$^{-1}$ (C=O of pyridone), 1700–1710 cm$^{-1}$ (C=O of ester).

EXAMPLE 25

3,5-Bis-ethoxycarbonyl-6-methyl-2-pyridone (25): Ethylcyanoacetate (2.26 g, 0.02 mol) was added to a NaOEt solution (prepared from 0.46 g of sodium metal in 50 ml EtOH), followed by compound 1 (3.72 g, 0.02 mol). The solution was refluxed for 12 hours. Shiny, light-yellow crystals precipitated out after 18 hours of standing at room temperature. After decolorizing with Nuchar activated carbon, white crystals of 3,5-bis-ethoxycarbonyl-6-methyl-2-pyridone were obtained: 1.45 g, 29% yield; mp=195°–197° C.; NMR (DMSO-d$_6$) δ 1.1–1.5 (t, 6H), 2.6 (s, 3H), 4.1–4.5 (q, 4H), 8.6 (s, 1H), 12.6 (NH); IR (KBr) 1660 cm$^{-1}$ (C=O of pyridone), 1700 cm$^{-1}$ and 1720 cm$^{-1}$ (C=O of ester).

EXAMPLE 26

Ethyl 3-cyano-6-methyl-2-pyridone-4-carboxylate (26): Based on the method described by Fuchs et al., *Chem. Abst.*, 72, 100533 f (1970), a solution of sodium metal (1.15 g, 0.05 g-atom) in ethanol (32 ml) was added to acetone (2.9 g, 0.05 mol) and diethyloxalate (7.31 g, 0.05 mol) in ethanol (10 ml), followed by cyanoacetamide (2.77 g, 0.033 mol) in water (15 ml). The solution was heated on an oil bath at 60°–70° C. for 30 minutes with constant stirring. The solvent was removed under reduced pressure giving an orange solid which was dissolved in a small amount of water and acidified with 6N HCl to pH=2, giving a yellow solid. After filtering and drying, a crude yield of 5.4 g (79%) was obtained. Decolorizing with Nuchar activated carbon gave light-yellow, needlelike crystals: 2.52 g, 24% yield; mp=215°–217° C.; NMR (DMSO-d$_6$) δ 1.2–1.5 (t, 3H), 2.4 (s, 1H), 4.2–4.6 (q, 2H), 6.6 (s, 1H); IR (KBr) 2240 cm$^{-1}$ (CN), 1640 cm$^{-1}$ (C=O of pyridone), 1720 cm$^{-1}$ (C=O of ester).

EXAMPLE 27

3-(N-imidazolyl-carbonyl)-6-methyl-2-pyridone (27): To 4 g (0.026 mol) of 6-methyl-2-pyridone-3-carboxylic acid in 25 ml DMF was added 5.3 g (0.033 mol) of carbonyldiimidazole. The mixture was heated to 55° C. with stirring for 2.5 hours. Bubbles and off-white precipitate were observed during this period. After filtering the solids, washing thoroughly with THF and drying in the vacuum dessicator for 18 hours, 4.7 g (89%) of the produce was obtained: mp=237°–239° C. with decomposition; NMR (DMSO-d$_6$) δ 2.3 (s, 3H), 3.4 (NH), 6.2–6.4 (d, 1H), 7.1 (d, 1H), 7.6 (d, 1H), 7.8–8.0 (d, 1H), 8.2 (d, 1H); IR (KBr) 1660 cm$^{-1}$ (C=O), 1700 cm$^{-1}$ (C=O).

EXAMPLE 28

5-(-N-imidazolyl-carbonyl)-2-pyridone (28): 6-Hydroxy-nicotinic acid (8.0 g, 0.06 mol) and carbonyldiimidazole (12.0 g, 0.074 mol) were heated at 55° C. for 4 hours in 50 ml DMF. After filtering and washing with ether and water, light-beige crystals of product were obtained: 4.2 g, 38% yield; mp=200°–200.5° C.; NMR (DMSO-d$_6$) δ 6.4 (d, 1H), 7.2 (s, 1H), 7.6–8.1 (m, 3H), 8.4 (s, 1H); IR (KBr) 1600 cm$^{-1}$, 1650–1680 cm$^{-1}$ (C=O of pyridone and imidazolide).

EXAMPLE 29

5-(N-imidazolyl-carbonyl)-3-cyano-6-methyl-2-pyridone (29): To 0.20 g (1.1 mmol) of 11 in 10 ml DMF was added carbonyldiimidazole (0.223 g, 1.4 mmol). The solution was stirred for 24 hours at room temperature. Dimethylformamide was stripped off under reduced pressure giving an oil which crystallized upon further drying. The solid was washed with water and dried in the vacuum dessicator. Yellow solids were obtained: 0.11 g, 40% yield; mp=237°–238° C. with decomposition; NMR (DMSO-d$_6$) δ 2.5 (s, 3H), 7.2 (d, 1H), 7.8 (d, 1H), 8.4 (2s, 2H); IR (KRr) 1670 cm$^{-1}$ (C=O of pyridone), 1710 cm$^{-1}$ (C=O of imidazolide).

EXAMPLE 30

5-(4,4-Dimethyl-2-oxazolin-2-yl)-2-pyridone (30): 2-Methyl-2-amino-1-propanol (0.94 g, 0.011 mol) and compound 29 (2.0 g, 0.011 mol) were refluxed for 12 hours in 100 ml DMF. The solvent was stripped off giving an oil which was washed with ether and CH$_2$Cl$_2$ and further dried under reduced pressure. Thionyl chloride (10 ml) was then added to the oil and the mixture stirred for 30 minutes. The thionyl chloride suspension was added dropwise to 100 ml of 15% NaOH, cooled in an ice-bath, and more base was added until pH reached 7–8. Insoluble materials were filtered off. The filtrate was extracted with CH$_2$Cl$_2$ (2×50 ml) and the organic extract was separated out, dried over MgSO$_4$ and concentrated to an oil, which crystallized on standing. Trituration with EtOAc removed the yellow color and gave 0.49 g (23% yield) of white crystalline solid: mp=172°–173° C.; NMR (DMSO-d$_6$) δ 1.4 (s, 6H), 4.0 (s, 2H), 6.5–6.7 (d, 1H), 8.0–8.2 (m, 2H); IR (KBr) 1600 cm$^{-1}$, 1650–1680 cm$^{-1}$ (C=O of pyridone and C=N).

EXAMPLE 31

Ethyl 2-pyridone-5-carboxylate (31): To 6-hydroxynicotinic acid (1.0 g, 7.19 mmol) suspended in absolute ethanol (EtOH) (10 ml) was added dropwise SOCl$_2$ (0.55 ml, 7.5 mmol). The reaction mixture was warmed at reflux for 4 hours and concentrated under reduced pressure. The white solid obtained was stirred in hexanes, filtered, and dried to give the product as the hydrochloride salt (1.38 g, 94%), mp=117°–124° C., NMR (DMSO-d$_6$) δ 1.45 (t, J=7 Hz, 3H), 4.27 (q, J=7 Hz, 2H), 6.35–8.17 (m, 3H).

Employing the above described procedure and starting with the appropriate alcohol, the following compounds were prepared.

EXAMPLE 32

Methyl 2-pyridone-5-carboxylate (32): mp 169°–170° C.; NMR (DMSO-d$_6$) δ 3.8 (s, 3H), 6.45 (d, 1H), 7.91 (m, 2H).

EXAMPLE 33

Isopropyl 2-pyridone-5-carboxylate (33): mp 123°–127° C.; NMR (DMSO-d$_6$) δ 1.29 (d, ,6H), 5.07 (bm, 1H), 6.38 (d, 1H), 7.87 (m, 2H).

EXAMPLE 34

Ethyl 3-cyano-5,6-dimethyl-2-pyridone-4-carboxylate (34): Using the methods of Example 26, a solution of NaOEt was prepared by dissolving sodium (1.15 g, 50 mmol) in absolute EtOH (50 ml). This solution plus an EtOH (2 ml) wash was added to a solution of methylethyl ketone (4.5 ml, 50 mmol) and diethyl oxalate (6.8 ml, 50 mmol) in EtOH (15 ml). A solution of cyanoacetamide (2.77 g, 33 mmol) in water (15 ml) was added and the reaction mixture warmed at 65° C. for 35 minutes. The reaction mixture was concentrated under reduced pressure, taken up in $H_2O$ (250 ml), filtered, and the filtrate acidifed with 6N HCl. Filtration afforded a mixture of the 5,6-dimethyl and 6-ethyl compounds. From the filtrate the product crystallized (400 mg, 6%) as a bright yellow solid, mp=172°–176° C., NMR (DMSO-$d_6$) δ 1.33 (t, J=7 Hz, 3H), 192 (s, 3H), 2.33 (s, 3H), 4.42 (q, J=7 Hz, 2H), IR (KBr) 2230, 1740, 1650 cm$^{-1}$.

Employing the procedure of Example 22 and starting with the appropriate ketone, oxalate, alkoxide, and alcohol, the following compounds were prepared.

EXAMPLE 35

Ethyl 3-cyano-6-cyclopropyl-2-pyridone-4-carboxylate (35): mp 210°–212° C.; NMR (DMSO-$d_6$) δ 1.33 (t, J=7 Hz, 3H), 1.17 (m, 4H), 2.01 (m, 1H), 4.38 (q, J=7 Hz, 2H), 6.35 (s, 1H); IR (KBr) 2230, 1725, 1640 cm$^{-1}$.

EXAMPLE 36

Methyl 3-cyano-6-methyl-2-pyridone-4-carboxylate (36): mp 233°–234° C.; NMR (DMSO-$D_6$) δ 2.35 (s, 3H), 3.92 (s, 3H), 6.58 (s, 1H); IR (KBr) 2230, 1740, 1670 cm$^{-1}$.

EXAMPLE 37

Isopropyl 3-cyano-6-methyl-2-pyridone-4-carboxylate (37): mp 216.9° C. (dec); NMR (DMSO-$d_6$) δ 1.33 (d, J=6 Hz, 6H), 2.33 (s, 3H), s.15 (m, 1H), 6.50 (s, 1H); IR (KBr) 2230, 1735, 1650 cm$^{-1}$.

EXAMPLE 38 sec-Butyl 3-cyano-6-methyl-2-pyridone-4-cArboxylate (38): mp 158.7° C.

The described compounds are active inotropic or cardiotonic agents. They have been found to increase the contractile force of the heart while having minimal effects on blood pressure and heart rate and can be used in treating patients with diseased hearts for the purpose of increasing cardiac efficiency through a selective increase in the cardiac contractile force.

The cardiotonic activity of the compounds was established using the following test procedure:

Male Hartley strain guinea pigs (250–500 g body weight), obtained from Hilltop Lab Animals (Scottdale, PA), were stunned by a blow to the head and the left atria removed and rinsed in a modified Kreb's-Henseleit buffer. The buffer was continuously gassed with 95% oxygen and 5% carbon dioxide and was composed of the following: NaCl, 118 mM; KCl, 4.7 mM; $MgSO_4$, 1.2 mM; $KH_2PO_4$, 1.2 mM; $CaCl_2$, 1.25 mM; $NaHCO_3$, 25 mM; $Na_2EDTA$, 0.03 mM and D-glucose, 11 mM. The left atria were placed through one end of the atrial appendage by a platinum hook connected to a fine gold chain and pierced at the other end of the appendage by a partially shielded platinum hook fixed to a glass rod.

The glass rod and atrium were suspended in a 30 ml water-jacketed tissue bath containing the Kreb's buffer at 33° C. Also connected to the glass rod was a second shielded platinum wire which was adjusted so that a 3–5 mm length of an unshielded portion of the wire was in contact with the atrium very near to the first shielded wire. Both platinum wires were connected to a Grass CCU1A constant current unit and a current was applied by a Grass S44 stimulator to drive the atrium by means of "point" stimulation. The parameters of stimulation were 1–3 mAmps, 1.5 Hz and 5 msec pulse duration. Each tissue was stretched to an initial resting tension of 1.0 g without further readjustment and wash periodically with fresh Kreb's buffer over a one-hour interval.

Developed tension was measured from a Statham UC-3 force transducer connected to the gold chain and recorded on a Gould 2800S recorder. The force signal was also passed to the A/D converter of a MINC-23 computer where the force signal was derivatized to calculate several characteristics of the contractile waveform.

After the one-hour equilibration period, test compounds were added cumulatively to the bath in small volumes (10–100 ul) at 10-minute intervals beginning at concentrations of $10^{-7}M$ and increasing by log or ½ log units until a concentration of $3 \times 10^{-3}M$ was reached.

Using the described procedure, the change in tension in milligrams is measured. An increase in tension indicates a greater contractile force. The increase in tension produced by several representative compounds is recorded in the following table in which $ED_{20}$ represents the dose of the compounds which causes a 20% increase in contractile force; GPLA is "guinea pig left atrium"; and IA is the intrinsic activity as contractile force in comparison to isoproterenol (1).

TABLE I

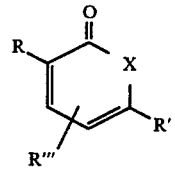

| | X | R | R' | R''' | GPLA $ED_{20}$ (μm) | IA |
|---|---|---|---|---|---|---|
| 1 | NH | H | H | 5-$CO_2Et$ | 1285 | 0.50 |
| 2 | NH | H | H | 5-$CO_2Me$ | 1250 | 0.42 |
| 3 | NH | H | H | 5-$CO_2$—i-Pr | 137 | 0.80 |
| 4 | NH | CN | Me | 5-$CO_2Et$ | 39 | 0.80* |
| | | | | | 24 | 0.63+ |
| 5 | NH | CN | Me | 5-$CO_2Me$ | 427 | 0.05+ |
| 6 | NH | CN | Me | 5-$CO_2CH_2Ph$ | 11 | 0.48* |
| 7 | NH | CN | Me | 5-$CO_2$—i-Pr | 15 | 0.60* |

TABLE I-continued

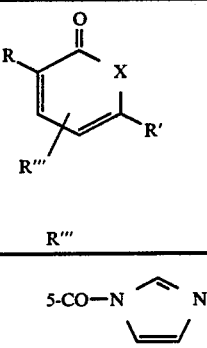

| | X | R | R' | R''' | GPLA ED$_{20}$ (μm) | IA |
|---|---|---|---|---|---|---|
| 8 | NH | CN | Me | 5-CO-N⟨imidazole⟩ | 45 | 0.92* |
| 9 | NH | CO-N⟨imidazole⟩ | Me | H | 180 | 1.0* |
| 10 | NH | CO$_2$Et | Me | 5-CO$_2$Et | 130 | 0.40* |
| 11 | NH | CO$_2$Me | Me | 5-CO$_2$Et | 475 | 0.30* |
| 12 | NH | H | H | 5-CO-⟨4,4-dimethyloxazoline⟩ | 826 | 0.58* |
| 13 | NH | H | H | 5-CO-N⟨imidazole⟩ | 267 | 1.12* |
| 14 | NH | CN | Me | 4-CO$_2$Et, 5-Me | 116 | 0.84* |
| 15 | NH | CN | Me | 4-CO$_2$Et | 1209 | 0.51* |
| 16 | O | CO$_2$Me | Me | 5-CO$_2$Et | 97 | 0.45* |
| 17 | NH | CN | Me | 5-CO$_2$(CH$_2$)$_3$CH$_3$ | 18 | 0.45* |
| 18 | NH | CN | Me | 5-CO$_2$(CH$_2$)$_7$CH$_3$ | 1207 | 0.5* |
| 19 | NH | CN | Me | 5-CO$_2$CH$_2$-(3-methylphenyl) | 173 | 0.93* |
| 20 | NH | CN | Me | 5-CO$_2$CH$_2$-cyclopropyl | 12 | 0.77* |
| 21 | NH | CN | Me | 5-CO$_2$CH$_2$-cyclohexyl | 613 | 0.25* |
| 22 | NH | CN | Me | 5-CO$_2$CH(CH$_2$CH$_3$)(CH$_3$) | 24 | 0.35* |
| 23 | NH | CN | Me | 4-CO$_2$CH$_2$CH(CH$_3$)$_2$ | 17 | 0.55* |
| 24 | NH | CN | Me | 5-CO$_2$CH$_2$-(2-furyl) | 21 | 0.33* |

TABLE I-continued

| | X | R | R' | R''' | GPLA ED$_{20}$ (μm) | IA |
|---|---|---|---|---|---|---|
| 25 | NH | CN | | 4-CO$_2$—Et (cyclopropyl) | 74 | 1.03* |
| 26 | NH | CN | Me | 4-CO$_2$Me | 450 | 0.85* |
| 27 | NH | CN | Me | 4-CO$_2$—i-Pr | 649 | 0.6* |
| 28 | NH | CN | Me | 4-CO$_2$—CH(CH$_3$)(CH$_2$CH$_3$) | 120 | 0.66* |
| 29 | NH | CN | Me | 5-CO$_2$—cyclopentyl | 28.5 | 0.41* |

\* = Pre-treatment with Reserpine
+ = Pre-treatment with Propranolol

EXAMPLE 39

Preparation of β-Keto-Ester Enamines

Using the procedure of Lesher et al. as described in U.S. Pat. No. 4,297,360, a solution of the appropriate ester of acetoacetic acid (0.05 mole) and dimethylformamide dimethyl acetal (0.15 mole) was stirred at room temperature for 30 minutes to 2 hours. In some cases, refluxing for 30 minutes to 1 hour was necessary to complete the reaction. Concentration under reduced pressure gave a yellow-orange or brown oily residue. Vacuum distillation of the crude residue gave a yellow oil as the desired product. For those keto-esters with a cyclic, aromatic, or heterocyclic ring in the ester function, the crude oil was used without further purification since decomposition of product was observed after vacuum distillation. $^1$H-NMR analysis of the product showed the disappearance of the singlet peak at 3.4–3.6 ppm (2H) and the appearance of a sharp singlet at 7.6–7.8 ppm (1H) and a large singlet at 3.0–3.2 ppm (6H).

The pyridone esters were prepared as previously described using the enamine in place of the analogous enol-ether.

Employing this procedure, the following compounds were prepared.

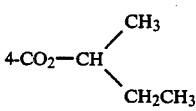

| Pyridones | GPLA (* = +R, + = +Prop) ED$_{20}$ (μm) | Max IA |
|---|---|---|
| R$_1$ = CN, R$_2$ = H, R$_4$ = Me, R$_3$ = CO$_2$Bn | 11.0 | 0.48* |
| R$_1$ = R$_2$ = R$_4$ = H, R$_3$ = (morpholinyl group) | 826.0 | 0.58* |
| R$_1$ = CN, R$_2$ = H, R$_4$ = CH$_3$, R$_3$ = CO$_2$CH$_2$-cyclopropyl | 12.0 | 0.76 |
| R$_1$ = CN, R$_2$ = H, R$_4$ = CH$_3$, R$_3$ = CO$_2$CH$_2$-cyclohexyl | (17) (1208) | 0.25* |

-continued

[Structure: Pyridone core with R1, R2, R3, R4 substituents; 2-oxo-pyridine with NH]

| Pyridones | GPLA (* = +R, + = +Prop) | |
|---|---|---|
| | $ED_{20}$ (μm) | Max IA |
| $R_1$ = CN, $R_2$ = H, $R_4$ = $CH_3$, $R_3$ = $CO_2CH_2$-(o-tolyl) | 173.0 | 0.93* |
| $R_1$ = CN, $R_2$ = H, $R_4$ = $CH_3$, $R_3$ = $CO_2CH_2$-(2-furyl) | 21.0 | 0.34* |
| $R_1$ = CN, $R_2$ = H, $R_4$ = $CH_3$, $R_3$ = $CO_2$-cyclopentyl | 28.5 | 0.41* |
| $R_1$ = CN, $R_2$ = H, $R_4$ = $CH_3$, $R_3$ = $CO_2CH_2CH_2Cl$ | 19.5 | 0.41* |
| $R_1$ = CN, $R_2$ = H, $R_4$ = H, $R_3$ = $CO_2$-cyclohexyl | 457.0 | 0.46* |
| $R_1$ = CN, $R_2$ = H, $R_4$ = Me, $R_3$ = CONH-iPr | 1172.0 | 0.57* |
| $R_1$ = CN, $R_2$ = H, $R_4$ = Me, $R_3$ = $CO_2$-allyl | 10.0 | 0.63* |
| $R_1$ = CN, $R_2$ = H, $R_4$ = $CH_3$, $R_3$ = $CO_2$-(cyclohex-3-enyl) | 34.4 | 0.33 |
| $R_1$ = CN, $R_2$ = H, $R_4$ = $CH_3$, $R_3$ = $CO_2CH_2$-(1,3-dioxan-2-yl) | 125.0 | 0.50 |
| $R_1$ = CN, $R_2$ = H, $R_4$ = Me, $R_3$ = $CO_2$-(tetrahydrofuran-3-yl) | 158.0 | 0.79 |
| $R_1$ = CN, $R_2$ = H, $R_4$ = $CH_3$, $R_3$ = $CO_2CH(CH_3)CO_2CH_3$ | 74.0 | 0.72 |
| $R_1$ = CN, $R_2$ = H, $R_4$ = $CH_3$, $R_3$ = $CO_2CH(CH_3)$-cyclopropyl | 29.5 | 0.37 |
| $R_1$ = CN, $R_2$ = H, $R_4$ = $CH_3$, $R_3$ = $CO_2CH_2$-cyclobutyl | 47.0 | 0.37 |
| $R_1$ = CN, $R_2$ = H, $R_4$ = $CH_3$, $R_3$ = $CO_2CH_2CH=CH_2CH_3$ | 28 | 0.47 |
| $R_1$ = CN, $R_2$ = H, $R_4$ = $CH_3$, $R_3$ = $CO_2CH_2C\equiv CH$ | 78 (136,19) | 0.65 |

-continued

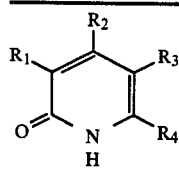

| Pyridones | GPLA (* = +R, + = +Prop) | |
|---|---|---|
| | ED$_{20}$ (μm) | Max IA |
| | 94 | 0.93 |

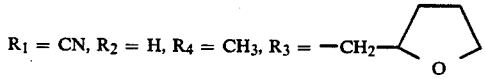

R$_1$ = CN, R$_2$ = H, R$_4$ = CH$_3$, R$_3$ = —CH$_2$—⟨furan-THF⟩

R$_1$ = CN, R$_2$ = H, R$_4$ = CH$_3$, R$_3$ = —CH$_2$CH$_2$OCH$_3$

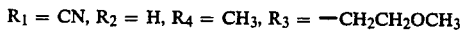

R$_1$ = CN, R$_2$ = H, R$_4$ = CH$_3$, R$_3$ = —CH$_2$—⟨C$_6$H$_4$⟩—OCH$_3$

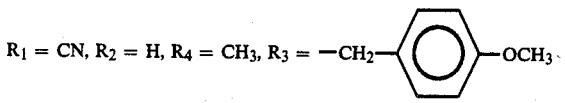

R$_1$ = CN, R$_2$ = H, R$_4$ = CH$_3$, R$_3$ = —CH$_2$—⟨dioxolane⟩

R$_1$ = CN, R$_2$ = H, R$_4$ = CH$_3$, R$_3$ = —CO$_2$CH(CH$_3$)CO$_2$CH(CH$_3$)$_2$
R$_1$ = CN, R$_2$ = H, R$_4$ = CH$_3$, R$_3$ = —CO$_2$CH(CH$_3$)CO$_2$Et
R$_1$ = CN, R$_2$ = H, R$_4$ = CH$_3$, R$_3$ = —CO$_2$CH$_2$CH=CHPh

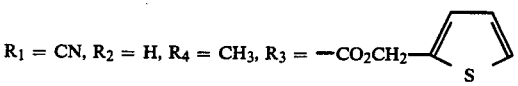

R$_1$ = CN, R$_2$ = H, R$_4$ = CH$_3$, R$_3$ = —CO$_2$CH$_2$—⟨thienyl⟩

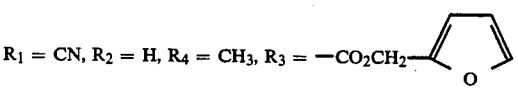

R$_1$ = CN, R$_2$ = H, R$_4$ = CH$_3$, R$_3$ = —CO$_2$CH$_2$—⟨furyl⟩

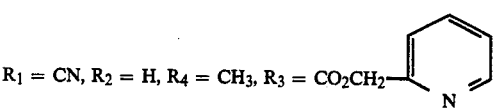

R$_1$ = CN, R$_2$ = H, R$_4$ = CH$_3$, R$_3$ = CO$_2$CH$_2$—⟨pyridyl⟩

What is claimed is:

1. A compound of the formula

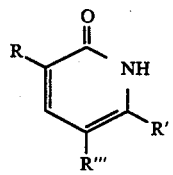

wherein R is cyano, R' is methyl, and R''' is —COOR'', where R'' is —(W)nY wherein W is —CH$_2$, n is 1, Y is 2 or 3 pyridyl.

2. A method of treating or relieving the symptoms associated with impaired ventricular myocardial contractility in a patient by providing a positive inotropic effect comprising administering to a patient in need of such treatment a therapeutically effective amount of a compound of the formula

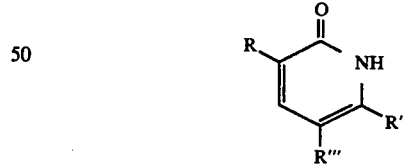

wherein R is cyano, R' is methyl, and R''' is —COOR'' where R'' is —(W)nY wherein W is —CH$_2$, n is 1, Y is 2 or 3 pyridyl.

* * * * *